United States Patent
Johnson

(10) Patent No.: US 10,130,284 B2
(45) Date of Patent: Nov. 20, 2018

(54) METHOD AND DEVICE FOR MEASURING A COMPONENT IN EXHALED BREATH

(71) Applicant: Circassia AB, Uppsala (SE)

(72) Inventor: Hans Peter Starck Johnson, Stockholm (SE)

(73) Assignee: Circassia AB, Uppsala (SE)

( * ) Notice: Subject to any disclaimer, the term of this patent is extended or adjusted under 35 U.S.C. 154(b) by 428 days.

(21) Appl. No.: 14/366,885

(22) PCT Filed: Dec. 20, 2012

(86) PCT No.: PCT/SE2012/051452
§ 371 (c)(1),
(2) Date: Jun. 19, 2014

(87) PCT Pub. No.: WO2013/095284
PCT Pub. Date: Jun. 27, 2013

(65) Prior Publication Data
US 2014/0358019 A1    Dec. 4, 2014

Related U.S. Application Data

(60) Provisional application No. 61/579,026, filed on Dec. 22, 2011.

(30) Foreign Application Priority Data

Dec. 22, 2011    (SE) ..................... 1151262

(51) Int. Cl.
*A61B 5/08*        (2006.01)
*A61B 5/097*       (2006.01)
(Continued)

(52) U.S. Cl.
CPC .............. *A61B 5/082* (2013.01); *A61B 5/097* (2013.01); *G01N 27/26* (2013.01); *G01N 33/497* (2013.01)

(58) Field of Classification Search
CPC .............................. A61B 5/082; A61B 5/097
See application file for complete search history.

(56) References Cited

U.S. PATENT DOCUMENTS 4,248,245 A * 2/1981 Kempin ............. G01N 33/4972
340/576
5,739,412 A    4/1998 Stock et al.
(Continued)

FOREIGN PATENT DOCUMENTS

DE    102009038237         3/2011
DE    102009038237 A1      3/2011
(Continued)

OTHER PUBLICATIONS

Extended European Search Report and Search Opinion for corresponding European Application No. 12859942.0 dated Jun. 29, 2015.
(Continued)

*Primary Examiner* — Meredith Weare
(74) *Attorney, Agent, or Firm* — Renner, Otto, Boisselle & Sklar, LLP

(57) ABSTRACT

A device for measuring a component in exhaled breath comprising an inlet (32) for receiving exhaled breath, a buffer chamber (31). A first fluid conduit (34a) is in fluid connection with the inlet and adapted to lead a first portion (I') of the exhaled breath to the buffer chamber. The buffer chamber comprises an outlet (37) for discarding a first part of exhaled breath received from the first fluid conduit and the buffer chamber is configured to buffer a second part of exhaled breath received from the first fluid conduit. The device comprises a second fluid conduit (34b) in fluid connection with the inlet and adapted to lead a second portion (I") of the exhaled breath to be discarded, and a (Continued)

sensor (63) for measuring a component in the exhaled breath buffered in the buffer chamber.

20 Claims, 3 Drawing Sheets

(51) Int. Cl.
 *G01N 33/497* (2006.01)
 *G01N 27/26* (2006.01)

(56) References Cited

U.S. PATENT DOCUMENTS

| | | | |
|---|---|---|---|
| 6,582,376 B2* | 6/2003 | Baghdassarian | A61B 5/097 |
| | | | 600/529 |
| 7,101,340 B1 | 9/2006 | Braun | |
| 2002/0193698 A1 | 12/2002 | Moilanen et al. | |
| 2003/0134427 A1 | 7/2003 | Roller et al. | |
| 2004/0039295 A1* | 2/2004 | Olbrich | A61B 5/0205 |
| | | | 600/538 |
| 2004/0077093 A1 | 4/2004 | Pan | |
| 2004/0082872 A1* | 4/2004 | von Bahr | A61B 5/0803 |
| | | | 600/532 |
| 2006/0178592 A1* | 8/2006 | Nason | A61B 5/0803 |
| | | | 600/532 |
| 2006/0200037 A1 | 9/2006 | Falasco | |
| 2008/0107569 A1 | 5/2008 | Stefano et al. | |
| 2008/0245366 A1 | 10/2008 | Lee | |
| 2010/0031730 A1* | 2/2010 | Van Uitert | A61B 5/082 |
| | | | 73/23.3 |
| 2010/0081955 A1 | 4/2010 | Wood, Jr. et al. | |
| 2010/0185112 A1 | 7/2010 | Van Kesteren et al. | |
| 2010/0262034 A1 | 10/2010 | Kawata et al. | |
| 2011/0066060 A1* | 3/2011 | von Bahr | A61B 5/0803 |
| | | | 600/532 |
| 2014/0180156 A1* | 6/2014 | Ku | G01N 1/2205 |
| | | | 600/532 |

FOREIGN PATENT DOCUMENTS

| | | |
|---|---|---|
| EP | 0904729 A1 | 3/1999 |
| JP | 2006518617 | 8/2006 |
| JP | 2009172347 | 8/2009 |
| JP | 2010509586 | 3/2010 |
| JP | 2010249556 | 11/2010 |
| WO | 9843539 A1 | 10/1998 |
| WO | 2004073779 | 9/2004 |
| WO | WO 2008056985 A1 * | 5/2008 ........... G01N 33/497 |
| WO | 2011101776 A1 | 8/2011 |

OTHER PUBLICATIONS

International Search Report from corresponding International Application No. PCT/SE2012/051452, dated Apr. 5, 2013.
Office Action for corresponding Japanese Application No. 2014-548738 dated Oct. 28, 2016 and its English translation.
Office Action for corresponding Japanese Application No. 2014-548738 dated Feb. 24, 2017 and its English translation.

* cited by examiner

METHOD AND DEVICE FOR MEASURING A COMPONENT IN EXHALED BREATH

TECHNICAL FIELD

The invention relates generally to a device and method for measuring concentrations in exhaled breath.

BACKGROUND

Inhaled ambient air, on average contains about 78% nitrogen, 21% oxygen, 0.96% argon and 0.04% carbon dioxide, helium, water, and other gases. The exhaled breath contains approximately 4% to 5% more carbon dioxide and 4% to 5% less oxygen than was inhaled. Furthermore, exhaled breath contains about 5% water vapor, and some parts per million (ppm) of hydrogen, carbon monoxide, ammonia, acetone, methanol, ethanol and nitric oxide (NO).

The measured content of exhaled breath can reveal physiological information about a person, as many components of the exhaled breath are produced or altered by the cells of the lungs and the respiratory tract. The physiological information may for instance be used to diagnose pathological conditions or the effect of a particular treatment. NO is an example of a component which can be used as an indicator for inflammation.

Endothelial cells on the inner surface of blood vessels, nerve cells and inflammatory cells produce NO in the body. In the respiratory system, alveolar cells, the respiratory tract epithelium or another type of cells in contact with the lungs or the airways of the respiratory tract produce endogenous NO. This NO is secreted into the air in the respiratory ducts and/or lungs and can be measured in exhaled air.

An evaluation of the production of endogenous NO in the lungs and respiratory ducts provides a measurement of the condition and/or function of the lungs and respiratory ducts. The NO measured in the exhaled air is unlikely to emanate from other organs in the body since NO produced in other locations of the body would immediately bind to the blood's hemoglobin and then be broken down subsequently.

NO is formed endogenously along the whole breathing pathway, i.e. in the oral cavity, in the sinuses, in the nose, in the trachea past the larynx, in the bronchia and within the "free space" in the lungs, as well as in the inner blood-filled parts of the lungs. As the diagnostic purpose is directed to the condition of the lungs and/or respiratory tract, the NO generated in the volume of the mouth, nose, throat and bronchus are of less interest and should advantageously be disregarded. The volume of the mouth, nose, throat and bronchus is known as the "dead space" and is typically approximately 2 ml per kg of body weight, although certain deviations can occur with regard to physique, age, sex and the possible use of breathing aids such as tracheotomy or intubation tubing.

As the volume of the "dead space" should be disregarded there is a significant advantage from a diagnostic perspective with collecting a sample for NO measurement from the last part or portion of the exhalation. As the last part should be collected, the commencing phase is discarded by allowing a volume exceeding the volume of the "dead space" by a suitable factor to flow through the device before collecting a sample. Furthermore, it is advantageous to allow the exhalation flow from the patient to settle to a continuous flow, such that a steady level of exhaled NO is reached. The state which is sought after is known as a "plateau" of the exhalation.

The following paragraph comes from the American Thoracic Society (ATS)/European Respiratory Society (ERS) Recommendations for Standardized Procedures for the Online and Offline Measurement of Exhaled Lower Respiratory Nitric Oxide and Nasal Nitric Oxide, 2005, which is hereby incorporated by reference:

Online methods refer to exhalations where the expirate is continuously sampled by the NO analyzer, and the resultant NO profile versus time or exhaled volume, together with other exhalation variables (e.g., airway flow rate and/or pressure), is captured and displayed in real time. This enables the test administrator to monitor the exhalation to ensure conformation to the required flow rate and pressure parameters and the achievement of an adequate NO plateau. In the exhalation phase two factors are critical in ensuring reproducible and standardized measurements of lower respiratory tract exhaled NO: (1) exclusion of nasal NO and (2) standardization of exhalation flow rate. The exclusion of nasal NO is important in view of the high nasal NO levels relative to the lower respiratory tract. This nasal NO can enter the oral expiratory air via the posterior nasopharynx. Closure of the velopharyngeal. With biofeedback of expiratory pressure or flow rate, most subjects are able to maintain low flow rates that vary little from the desired target. In general, an exhalation is deemed adequate if the mean exhalation flow rate is 0.05 L/second (10%) during the time of the NO plateau generation, and instantaneous flow rate is not less than 0.045 L/second or greater than 0.055 L/second at any time during the exhalation. If it is not possible to keep within these values, the results should still be recorded and the failure to achieve this flow rate criterion noted in the record. The duration of exhalation must be sufficient; at least 4 seconds for children below 12 years and 6 seconds for children above 12 years and adults. This corresponds to an exhaled volume of at least 0.3 L in adults at an exhalation flow rate of 0.05 L/second to allow the airway compartment to be washed out and a reasonable plateau achieved. In general, patients can exhale comfortably up to 10 seconds, and this may be necessary for the achievement of a stable NO plateau. The plateau concentration in NO should be evaluated over a 3-second (0.15 L) window of the exhalation profile. A plateau is defined according to the following guidelines, two points, A and B, which should be chosen to define the first 3-second window in the exhaled concentration profile such that the absolute magnitude of A-B is less than 10%. The plateau concentration, FeNO, is then defined at the mean concentration over this 3-second window.

To meet the requirements of the ATS/ERS, a total of 0.15 L must be collected and analyzed during online NO measurement and a total of at least 0.3 L for an adult needs to be used to gather the 0.15 L to be measured, i.e. 0.15 L needs to be discarded.

U.S. Pat. No. 6,038,913 to Persson et al. discloses a device for collecting and separating the first exhalation volume from the "dead space" of the patient (and of the instrument) in a first chamber, whereafter the sample for measurement is collected in a different chamber having a volume of at least the required 0.15 L. The device thus takes a sample of at least 0.15 L from the plateau-region for analysis, as required by the ATS.

J. H. Green in "An introduction to human physiology", 3rd edition, 1966, Oxford University Press, London, Chapter 5 "Respiration", also discloses (especially in FIG. 99), the possibility to, during the exhalation, first fill an initial balloon with air from the "dead space" and a part of the alveolar air with a second balloon closed-off, and thereafter close-off the flow to the said initial balloon and collect the remaining exhaled air of the exhalation phase, which comprising the alveolar air, in a second balloon. In this case, the contents of oxygen and carbon dioxide are determined. In the filling of both these balloons, the patient breaths against a considerable resistance or back-pressure. Further, the balloon does not provide a distinct end-point determining the exhaled volume.

In the two examples of prior art devices above a chamber of 0.15 L is required for the sample collection, which creates a lower limit on the size of the device which must be considered to be a substantial design limitation.

SUMMARY

It is an object of the embodiments herein to address at least some of the problems and shortcomings outlined above by using an arrangement and method as defined in the attached claims.

A device for measuring a component in exhaled breath is provided. The device comprises an inlet for receiving exhaled breath, a buffer chamber, a first fluid conduit in fluid connection with the inlet and adapted to lead a first portion of the exhaled breath to the buffer chamber. The buffer chamber comprises an outlet for discarding a first part of exhaled breath received from the first fluid conduit. This first part may correspond to the dead space volume of the exhaled breath. The buffer chamber is configured to buffer a second part of exhaled breath received from the first fluid conduit. The second part may correspond to the "plateau" of the exhalation. The device further comprises a second fluid conduit in fluid connection with the inlet and adapted to lead a second portion of the exhaled breath to be discarded, and a sensor for measuring a component in the exhaled breath buffered in the buffer chamber. By discarding a portion of the exhaled breath a smaller sample can be measured which enables the construction of the device to be smaller.

The device and sensor could according to one embodiment be adapted to measure the content of NO as a component in the exhaled breath, but in other conceivable embodiments the sensor is a sensor adapted to determine the concentration of other components of the exhaled breath, such as carbon dioxide ($CO_2$) carbon monoxide (CO), ammonia ($NH_3$), acetone (($CH_3$)$_2$CO), methanol ($CH_3OH$) or ethanol ($C_2H_5OH$).

According to one embodiment of the device, the first fluid conduit has a first flow cross-section area, perpendicular to the direction of the flow in the first fluid conduit, and the second fluid conduit has a second flow cross-section area, perpendicular to the direction of the flow in the second fluid conduit. The second flow cross-section area is larger than the first flow cross-section area, which means that the discarded portion is larger than the portion collected to be measured. The first flow cross-section area could be at least one of: 0.5 times the area of the second flow cross-section area, 0.4 times the area of the second flow cross-section area, 0.3 times the area of the second flow cross-section area, 0.2 times the area of the second flow cross-section area, and 0.1 times the area of the second flow cross-section area.

According to one embodiment of the device the buffer chamber comprises a buffer conduit, wherein the outlet is arranged at a distal portion of the buffer conduit with respect to the inlet or the first fluid conduit.

According to one embodiment of the device, the buffer conduit has a cross-sectional dimension, perpendicular to the direction of the flow in the buffer conduit, having a length: less than $1/5$ of the length of the buffer conduit, less than $1/10$ of the length of the buffer conduit, less than $1/20$ of the length of the buffer conduit, less than $1/50$ of the length of the buffer conduit, less than $1/70$ of the length of the buffer conduit or less than $1/100$ of the length of the buffer conduit. By the buffer chamber being elongated by means of an elongated buffer conduit, the sample of exhaled breath collected in the buffer chamber is exchanged with minimal dilution.

According to one embodiment of the device, the buffer conduit comprises a maze, a meandering or at least one S-shape with the purpose of prolonging the flow path whilst keeping the buffer chamber compact and thus the outer measurements of the measurement device. The corners of the fluid conduit with at least one meander or S-shape may have rounded inside corners.

According to one embodiment of the device, the device further comprises a bifurcating wall adapted to separate the first fluid conduit from the second fluid conduit. The bifurcating wall may be adjustable such that the relationship between the first and second cross-section areas can be altered, for changing the amount of fluid flowing into the first and second fluid conduits, respectively. According to another embodiment the device comprises a replaceable adjustment member, for changing the amount of fluid flowing into the first and second fluid conduits, respectively. By enabling the adjustment of the bifurcating wall and/or replacement of the adjustment member, the measurement device could be adapted for individuals having respiratory tracts of different volume, and thus always measure exhaled breath representing the same relevant areas of the respiratory tract of the patient.

According to one embodiment of the device, the buffer chamber further comprises a first check valve, preferably placed at the outlet, such that fluid will be stopped from entering the buffer chamber during inhalation.

According to one embodiment of the device, the device further comprises a second check valve placed in the second fluid conduit such that fluid will be stopped from entering the second fluid conduit during inhalation According to one embodiment, the device comprises a sensor for sensing the amount of NO in a fluid flow. By using the buffer chamber disclosed herein, the device can be made very small.

According to one embodiment, the device further comprises a pump adapted to pump exhaled breath from the buffer chamber to the sensor.

According to one embodiment, the sensor is a sensor with a long response time requiring exposure to the exhaled breath longer time than the duration of an exhalation. An example of such a sensor is an electrochemical sensor. The sensor may have a response time of more than 5 seconds, or in the range of 5-15 s.

A method of measuring the concentration of a component in exhaled breath is further provided. The method, comprises the steps of;

receiving exhaled breath, leading a first portion of the exhaled breath through a first fluid conduit to a buffer chamber, leading a second portion of the exhaled breath through a second fluid conduit to be discarded, from the buffer chamber, discarding a first part of the first portion of the exhaled breath received from the first fluid conduit, in the buffer chamber, buffering a second part of the first portion of the exhaled breath received from the first fluid conduit, and measuring the concentration of the component in the exhaled breath buffered in the buffer chamber.

The method is preferably performed in a device as disclosed herein and the component may be NO.

According to one embodiment the method comprises the step of adjusting the flow of fluid into the first and second fluid conduits respectively. By adjusting the fluid flow, different time phases of the exhalation can be selected, which for example is required if a patient is unable to complete the full preferred three seconds of exhalation, or if a particular region of the respiratory tract is of special interest.

According to one embodiment, the NO measuring device further comprises an adjustment member, and the step of adjusting the flow of fluid comprises adjusting the adjustment member or replacing the adjustment member. The adjustment member could for example be a bifurcating wall, and the step of adjusting the adjustment member could comprises adjusting the bifurcating wall.

Further possible features and advantages of this solution will become apparent from the detailed description below.

BRIEF DESCRIPTION OF DRAWINGS

Some possible embodiments will now be described, by way of example, with reference to the accompanying drawings, in which.

DETAILED DESCRIPTION

Figure 1:
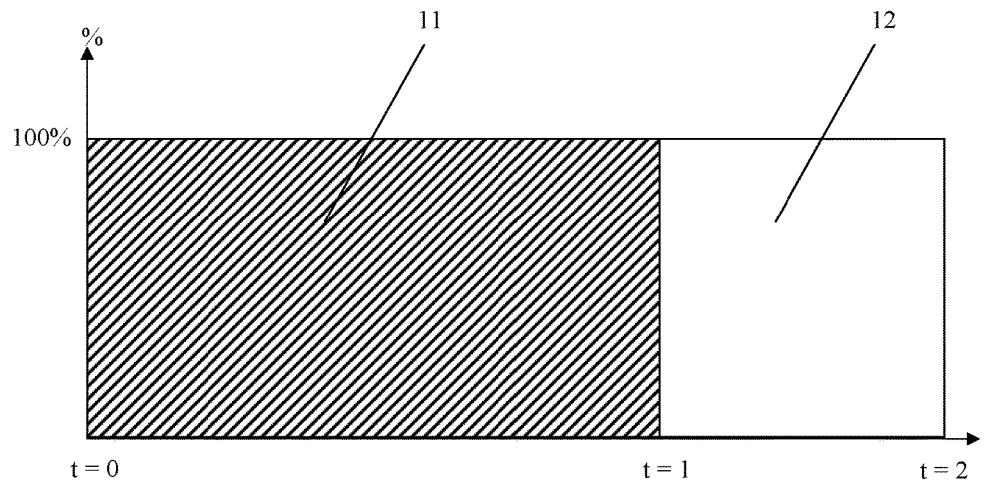
FIG. 1 is a graph of exhaled breath showing the dead space portion and the portion to be analyzed.

A device comprising a buffer chamber for use in a medical device for measurement of exhaled breath for diagnostic purposes is provided. The device comprises an inlet adapted to receive breath exhaled by the patient. A flow adjustment unit may be provided along the flow conduit leading from the inlet to the buffer chamber with the purpose of establishing a constant flow into the buffer chamber. The flow conduit further comprises a bifurcation separating the flow of exhaled breath into a first flow to be analyzed and a second flow to be discarded. By continuously discarding a portion of the flow by means of a bifurcation, a gas sample of less volume is collected. Collecting a gas sample of smaller volume enables the construction of a smaller and less energy consuming measurement device.

Buffered is to be understood as temporarily stored and buffer chamber is to be understood as a chamber suitable for temporary storage.

The portion of exhaled breath which is collected for analysis is led into an S-shaped fluid channel of the buffer chamber, creating an elongated portion of air which can be flowed over a sensor for measuring components of that particular portion of air. By creating an elongated air portion, the content in the buffer chamber is rapidly exchanged with as little dilution as possible, i.e. mixing of old exhaled breath or ambient air with the exhaled breath to be measured.

The device comprising the buffer chamber is adapted to be a part of an online measurement device for airway inflammatory diagnostics which according to one embodiment comprises a sensor with a long response time requiring exposure to the exhaled breath longer time than the duration of an exhalation, which requires the exhaled air to be buffered for creating a flow over the sensor which is extended in time. An example of such a sensor is an electrochemical sensor.

In the following, a detailed description of exemplifying embodiments of the buffer chamber will be given with reference to the accompanying drawings. A description of a measurement device adapted for measuring the NO content of exhaled breath using the buffer chamber will also be given as an example of an application of the device. However, it should be understood that the device may be used in combination with any type of sensor for the measurement of exhaled breath, such as a device for measurement of carbon dioxide ($CO_2$) carbon monoxide (CO), ammonia ($NH_3$), acetone (($CH_3$)$_2$CO), methanol ($CH_3OH$) or ethanol ($C_2H_5OH$). It will be appreciated that the figures described are for illustration only and are not in any way restricting the scope of the invention. Please note that any embodiment or part of embodiment as well as any method or part of method could be combined in any way. All examples herein should be seen as part of the general description and therefore possible to combine in any way in general terms. It should be noted that the units of the measurement device merely illustrate the nodes or functional units in a logical sense, although the skilled person is free to implement these functions in other locations of the conduit in practice as long as the function of the particular unit remains.

FIG. 1 shows a graph of a flow of exhaled breath over time (t). In embodiments where NO is to be measured for performing diagnostics related to the condition of the lungs and/or respiratory tract of the patient, the NO generated in the volume of the mouth, nose, throat and bronchus are of less interest and should advantageously be disregarded. This volume is known as "dead space" and is represented by the shaded part 11 in the graph. Apart from less interesting regions of the airways, the discarding of the dead space further takes care of the volume of ambient air present in the inlet conduit and the flow regulator of the measurement device. This volume typically represents 2-8 seconds (t=0-t=1) of the exhalation. Furthermore, an advantage with discarding the first part of the exhalation and performing analysis of a second subsequent part is that the exhalation flow from the patient is allowed to settle to a continuous flow which creates a more steady level of exhaled NO, a state which is known as a "plateau" of the exhalation.

After the dead space portion 11 of the exhaled breath, the second part representing the region of interest 12 is illustrated. The second part of breath to be measured is collected during the remainder of the exhalation. According to ATS/ERS guidelines, a plateau concentration of NO should be evaluated over a 3-second window of the exhalation profile. For an adult this means that at least 0.3 L needs to be used to gather 0.15 L to be analyzed, i.e. at least 0.15 L needs to be discarded. Part 11 represents the at least 0.15 L to be analyzed which is collected during the time t=1-t=2.

Figure 2:
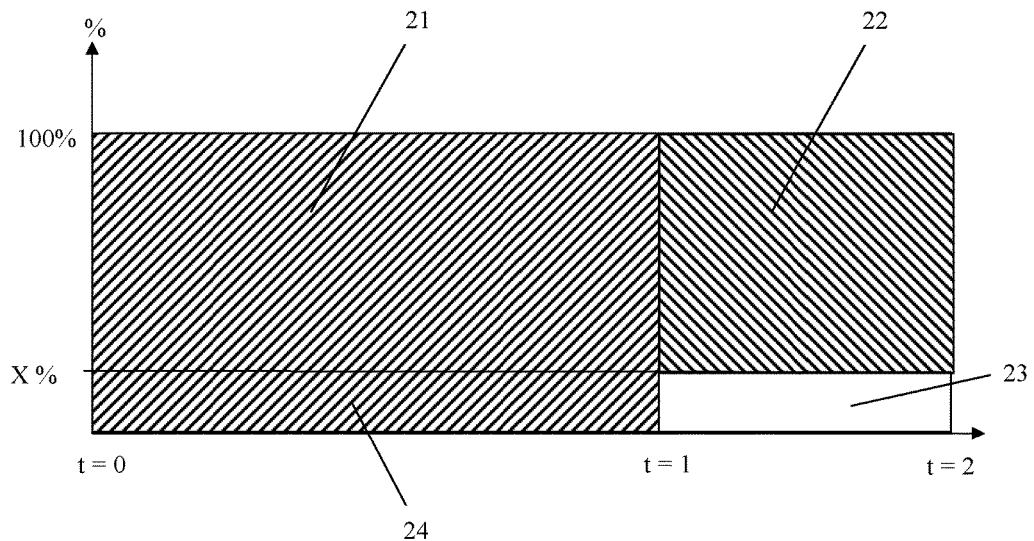
FIG. 2 is a graph of exhaled breath showing which portions of the exhaled breath that are to be discarded, FIG. 3 schematically shows a device according to one embodiment, FIG. 4 schematically shows a device according to another embodiment, and FIG. 5 schematically shows a device according to yet another embodiment.

FIG. 2 is a graph showing the different volumes of exhaled breath collected in a device comprising a buffer chamber according to embodiments disclosed herein. The first parts 21, 24, which are the parts of exhaled breath representing t=0-t=1, is in accordance with FIG. 1 representing the air from the dead space which is discarded prior to the collection of the sample to be measured. The sample portion 22 and 23 collected from time t=1 until t=2 is divided by means of the inlet of the buffer chamber (which is further disclosed with reference to FIGS. 3-5) into a first part 22 which is to be discarded and a second part 23, which is to be collected in the buffer chamber and subsequently analyzed. By continuously separating a portion 21 and 22 from the flow of exhaled breath, the portion 23 and 24 representing the exhaled breath may have a small volume. Further, by discarding a first part 24 of the portion representing the exhaled breath and buffering only the second part 23 for analysis the part 23 of the first portion to be analyzed can have a much smaller volume whilst still representing the entire interesting region of the patient's airways. The separated portion 24, 23 for analysis is denoted as X % of the total of 100% of the breath gas, and X % could according to one embodiment be ⅓ of the total volume of exhaled breath. However, according to other embodiments, the separated portion 24, 23 for analysis could be as much as 90%, 80% 60% 40% or 20% or as little as 1%, 2%, 4% or 10% of the total of exhaled breath.

Thus, according to the device disclosed herein a first portion 23 and 24 corresponding to X % of the exhaled breath is conducted to the buffer chamber. In the buffer chamber a first part 24 of the first portion of exhaled breath is discarded and a second part 23 of the first portion of exhaled breath is buffered for analysis. The second portion 21 and 22 of the exhaled breath is discarded.

Figure 3:
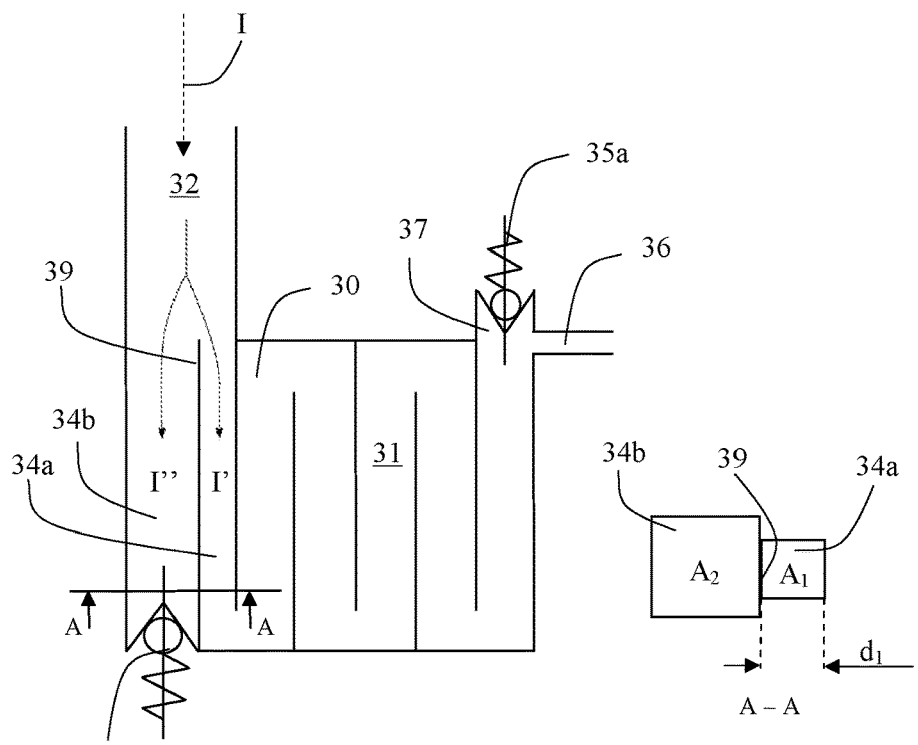

FIG. 3 shows the device having a buffer chamber 31 according to an embodiment in which the device comprises an inlet 32 adapted to receive an inflow I of breath exhaled by a patient. The inlet comprises a fluid conduit which transports the exhaled breath I towards a bifurcation 39 adapted to separate a first portion I' of the exhaled breath to be analyzed, from a second portion I" of the exhaled breath I, which is to be discarded. The bifurcation 39 divides the fluid conduit 39 into a first fluid conduit 34a and a second fluid conduit 34b. The second fluid conduit 34b guides the second portion I" of the exhaled breath to be discarded. According to the embodiment disclosed in FIG. 3, the second portion I" of the exhaled breath is a larger portion of the total of the exhaled breath I, for example ⅔. The second portion I" guided by the second fluid conduit 34b is discarded through a check valve 35b and further to the ambient air. The first portion I' of the exhaled air is separated by the bifurcation 39 and guided by the first fluid conduit 34a into the conduits making up the buffer chamber 31. The conduits making up the buffer chamber 31 creates an S-shaped lumen 30 in which the collected breath is buffered. From the buffer chamber a first part of the first portion of exhaled breath is discarded through the outlet 37 and a second part of the first portion of exhaled breath is buffered in the S-shaped lumen for analysis. The S-shaped lumen 30 creates an elongated portion of air which can be flowed over a sensor for measuring the NO content of that particular portion of air. By creating an elongated air portion, the content in the buffer chamber 31 is rapidly exchanged with as little dilution as possible, i.e. mixing of old exhaled breath or ambient air with the exhaled breath to be measured.

At the end of the S-shaped lumen 30, a fluid conduit 36 for leading the collected sample from the buffer chamber 31 to the sensor is placed. The collected breath is according to this embodiment pumped over the sensor by means of a pump, such as a membrane pump (further described under reference to FIG. 5). The other outlet 37 from the S-shaped lumen 30 of the buffer chamber 31 is the outlet 37 for discarding the first part of the exhaled breath corresponding to the dead space portion of the first portion I' through a check valve 35a and further to the ambient air. The purpose of the two check valves 35a, 35b is that no ambient air should leak into the fluid conduits/buffer chamber 31 of the device and dilute and/or contaminate the sample. Furthermore, the check valves 35a, 35b enable the inhalation of air through an NO-scrubber (which is further disclosed under reference to FIG. 5), which guarantees that exhaled NO originates from the airways of the patient and not from the ambient air. The ambient air could for example be contaminated by exhaust fumes from for example heavy vehicles, or residue anesthesia gases, which may be present in a hospital environment.

The section A-A shows the first fluid conduit 34a having a first flow cross-section area $A_1$, perpendicular to the direction of the flow in the first fluid conduit 34a, and the second fluid conduit 34b having a second flow cross-section area $A_2$, perpendicular to the direction of the flow in the second fluid conduit 34b being larger than the first flow cross-section area $A_1$. According to some embodiments, the first flow cross-section area $A_1$ is 0.5, 0.3, 0.2 or 0.1 times the area of the second flow cross-section area $A_2$. The section A-A further shows the first fluid conduit 34a having a cross-section distance d1 being perpendicular to the direction of the flow in the first fluid conduit 34a having a length less than ⅕, 1/10, 1/20, 1/50 or 1/100 of the length of the first fluid conduit 34a. The first fluid conduit is making up the buffer chamber 31 such that an elongated S-shaped lumen 30 is created for enabling the exchange of the air present in the buffer chamber with minimum dilution.

The first portion of fluid flow I' described in FIG. 3 represents the relevant fluid flow for measurement denoted as X % of the total flow in FIG. 2. Thus the first and second parts 24 and 23 from FIG. 2 represents the first portion of fluid flow I' of which the part 24 is the dead space sample which is discarded through the first check valve 35a. The second portion of fluid flow I" is in FIG. 2 represented by the parts 21 and 22 making up the portion from X % to 100% of the total exhaled breath. The second portion of fluid flow I" is to continuously be discarded through the second check valve 35b.

Thus, during operation of the device, exhaled breath is received at the inlet 32. A first portion I' of the exhaled breath is led through the first fluid conduit 34a to the buffer chamber 31. A second portion (I") of the exhaled breath is led through a second fluid conduit 34b to be discarded. From the buffer chamber, a first part of the first portion I' of the exhaled breath received from the first fluid conduit is discarded through the outlet 37, and a second part of the first portion I' of the exhaled breath received from the first fluid conduit is buffered in the buffer chamber for analysis.

Figure 4:
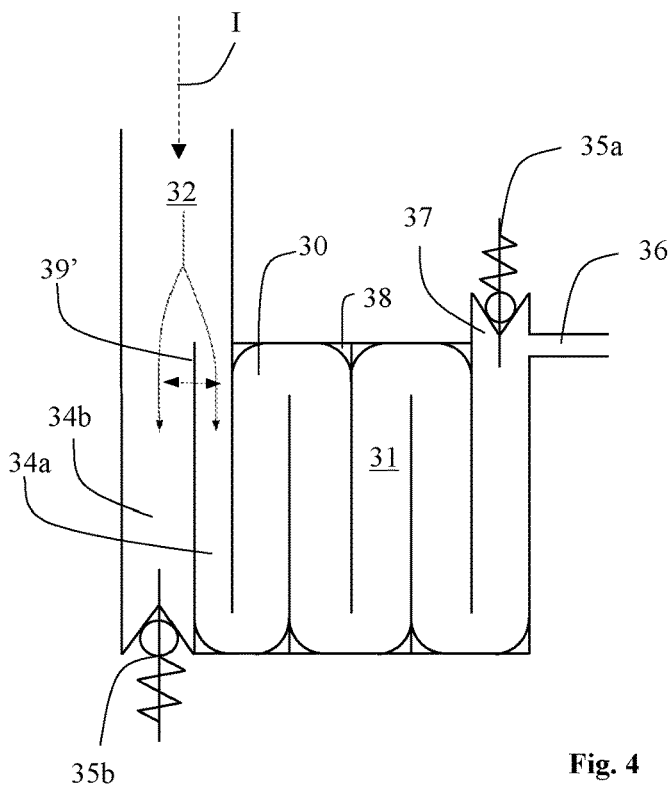

FIG. 4 shows an embodiment of the buffer chamber which is very similar to the embodiment described under reference to FIG. 3, with the difference that the S-shaped lumen 30 has rounded inside corners 38 which further improves the exchange of sample breath in the buffer chamber 31 as it reduces the risk that old sample breath and/or ambient air is trapped in the corners of the S-shaped lumen 30 of the buffer chamber 31 making the measurement more accurate. FIG. 4 furthermore shows the bifurcating wall 39', adapted to separate the first fluid conduit 34a from the second fluid conduit 34b, being adjustable such that the relationship between the first 34a and second 34b cross-section areas can be altered, for changing the amount of fluid flowing into the first 34a and second 34b fluid conduits, respectively. By enabling the adjustment of the bifurcating wall 39', different time phases of the exhalation can be selected, which for example is required if a patient is unable to complete the full preferred three seconds of exhalation, or if a particular region of the respiratory tract is of special interest.

Figure 5:
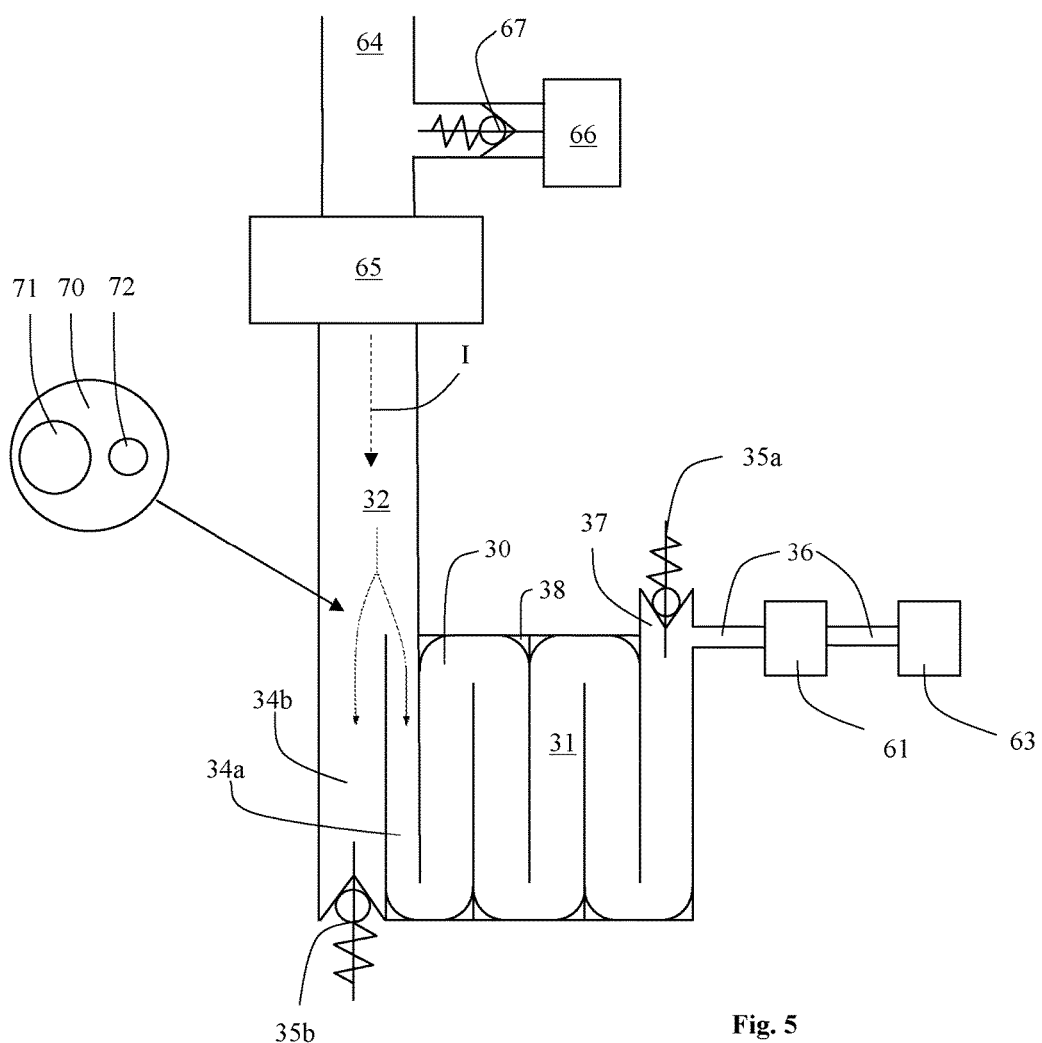

FIG. 5 shows a system overview comprising the device disclosed under reference to FIG. 4. The system overview comprises an inlet 64 into which the patient is to exhale and inhale. The first step of a measurement process is that the patient inhales through the inlet 64 so that the quality of the inhaled ambient air can be controlled. The inhaled air is according to the embodiment shown in FIG. 5 purified by means of a scrubber 66 removing $NO_x$ from the ambient air to establish that the entire concentration of NO comes from the patient's airways. The scrubber 66 could for example comprise potassium permanganate ($KMnO_4$) or potassium permanganate in combination with a suitable grade of carbon in granular form. The check valve 67 guarantees that air passes exclusively through the scrubber 66 during the inhalation phase, so that the all of the exhaled breath is led into the measurement device. The inflow of exhaled breath I is passed though a flow adjustment unit 65 adapted to normalize the flow of exhaled breath, such that a continuous flow representing the interesting regions of the patient's airways is achieved. After the flow adjustment unit 65 the flow of exhaled breath I is guided in accordance with the description made under reference to FIGS. 3 and 4.

The buffered exhaled breath is pumped from the buffer chamber 31 by means of a pump 61 placed along a fluid conduit 36 leading from the buffer chamber 31 to the sensor 63. The pump could for example be a membrane pump which makes sure that there is no back-flow through the pump contaminating the sample breath in the buffer chamber during the inhalation and/or exhalation phase. The sensor 63 is according to this embodiment an electrochemical sensor with a relatively slow response, leading to the need for the buffer chamber 31 and the pump 61. The pump flows the collected sample breath over the sensor at such a rate that the sensor 63 has sufficient time to respond to the NO content of the breath and thus being able to accurately sense inflammation in the airways indicated by the NO content.

FIG. 5 further shows an alternative embodiment of the bifurcating wall, in which the bifurcating wall comprises an adjustment member 70 comprising apertures 71, 72, the size of which determines the flow into the first 34a and second 34b fluid channels, respectively. The first aperture 72, adapted to lead a fluid flow into the first flow channel 34a, could have a cross-section area being 0.8, 0.5, 0.3, 0.2 or 0.1 times as large as the cross-section area of the second aperture 71. The adjustment member 70 could be replaceable to an adjustment member 70 having a different relationship between the sizes of the first and second apertures 72, 71. By enabling the adjustment of the sizes of the apertures 71, 72, different time phases of the exhalation can be selected, which for example is required if a patient is unable to complete the full preferred three seconds of exhalation, or if a particular region of the respiratory tract is of special interest.

Please note that any embodiment or part of embodiment as well as any method or part of method could be combined in any way. All examples herein should be seen as part of the general description and therefore possible to combine in any way in general terms. It should be noted that the units of the measurement device merely illustrate the nodes or functional units in a logical sense, although the skilled person is free to implement these functions in other locations of the conduit in practice as long as the function of the particular unit remains.

The invention claimed is:

1. A device for measuring a component in exhaled breath comprising;
   an inlet for receiving exhaled breath,
   a buffer chamber,
   a first fluid conduit in fluid connection with the inlet and adapted to lead a first portion of the exhaled breath to the buffer chamber, which buffer chamber comprises an outlet for discarding a first part of exhaled breath received from the first fluid conduit and wherein the buffer chamber is configured to buffer a second part of exhaled breath received from the first fluid conduit, the buffer chamber further comprising a first check valve, placed at the outlet, such that fluid will be stopped from entering the buffer chamber during inhalation,
   a second fluid conduit in fluid connection with the inlet and adapted to lead a second portion of the exhaled breath to be discarded,
   a partition positioned between the inlet and the first and second fluid conduits, the partition comprising a first open aperture configured to provide fluid flow into the first fluid conduit and a second open aperture configured to provide fluid flow into the second fluid conduit, the first open aperture being smaller than the second open aperture, the first and second apertures open simultaneously, the partition configured to divide the exhaled breath into respective portions at a constant proportion throughout the duration of the breath, and
   a sensor for measuring a component in the exhaled breath buffered in the buffer chamber.

2. The device according to claim 1, wherein the first fluid conduit has a first flow cross-section area, perpendicular to the direction of the flow in the first fluid conduit, and the second fluid conduit has a second flow cross-section area, perpendicular to the direction of the flow in the second fluid conduit, and wherein the second flow cross-section area is larger than the first flow cross-section area.

3. The device according to claim 2, wherein the first flow cross-section area is at least one of: 0.5 times the area of the second flow cross-section area, and 0.3 times the area of the second flow cross-section area.

4. The device according to claim 1, wherein the buffer chamber comprises a buffer conduit, and wherein the outlet is arranged at a distal portion of the buffer conduit with respect to the inlet or the first fluid conduit.

5. The device according to claim 4, wherein buffer conduit has a cross-sectional dimension, perpendicular to the direction of the flow in the buffer conduit, having a length less than: ⅕ of the length of the buffer conduit, ⅒ of the length of the buffer conduit, 1/20 of the length of the buffer conduit, 1/50 of the length of the buffer conduit, 1/70 of the length of the buffer conduit, or 1/100 of the length of the buffer conduit.

6. The device according to claim 4, wherein the buffer chamber comprises a buffer conduit with at least one meander or S-shape.

7. The device according to claim 6, wherein the corners of the buffer conduit with at least one meander or S-shape have rounded inside corners.

8. The device according to claim 1, wherein the device further comprises a second check valve placed in the second fluid conduit such that fluid will be stopped from entering the second fluid conduit during inhalation.

9. The device according to claim 1, wherein the device further comprises a pump adapted to pump exhaled breath from the buffer chamber to the sensor.

10. The device according to claim 1, wherein the component in exhaled breath is the amount of nitric oxide (NO).

11. The device according to claim 1, wherein the sensor is an electrochemical sensor.

12. The device according to claim 1, wherein the sensor is a sensor having a response time of more than 5 seconds, or in the range of 5-15 seconds.

13. The device according to claim 1, wherein the partition is replaceable.

14. The device according to claim 1, wherein the first open aperture has a cross-section that is 0.5-0.1 times as large as a cross-section of the second open aperture.

15. The device according to claim 1, further comprising a flow adjuster positioned between the inlet and the partition, the flow adjuster configured to normalize flow of the exhaled breath.

16. The device according to claim 1, wherein the partition comprises a major surface that faces a direction of flow of the exhaled breath in the inlet, the first and second apertures provided at and extending through the major surface.

17. A method of measuring the concentration of a component in exhaled breath, comprising the steps of:
   receiving exhaled breath at an inlet,
   dividing the exhaled breath into a first portion and a second portion at a partition positioned between the inlet and a first fluid conduit and second fluid conduit, the partition comprising a first open aperture configured to provide fluid flow into the first fluid conduit and a second open aperture configured to provide fluid flow into the second fluid conduit, the first open aperture being smaller than the second open aperture, the first and second apertures open simultaneously, the partition dividing the exhaled breath into respective first and second portions of the exhaled breath at a constant proportion throughout the duration of the breath,
   leading the first portion of the exhaled breath through the first fluid conduit to a buffer chamber,
   leading the second portion of the exhaled breath through the second fluid conduit to be discarded,
   from the buffer chamber, discarding a first part of the first portion of the exhaled breath received from the first fluid conduit at an outlet of the buffer chamber, the buffer chamber comprising a first check valve, placed at the outlet, such that fluid will be stopped from entering the buffer chamber during inhalation,
   in the buffer chamber, buffering a second part of the first portion of the exhaled breath received from the first fluid conduit, and
   measuring the concentration of the component in the exhaled breath buffered in the buffer chamber.

18. The method according to claim 17, wherein the partition is replaceable.

19. The method according to claim 17, wherein the first open aperture has a cross-section that is 0.5-0.1 times as large as a cross-section of the second open aperture.

20. The method according to claim 17, further comprising normalizing flow of the received exhaled breath prior to dividing the exhaled breath.

* * * * *